(12) United States Patent
Gangjee

(10) Patent No.: US 6,770,652 B2
(45) Date of Patent: Aug. 3, 2004

(54) MULTIPLE ACTING ANTI-ANGIOGENIC AND CYTOTOXIC COMPOUNDS AND METHODS FOR USING THE SAME

(75) Inventor: Aleem Gangjee, Allison Park, PA (US)

(73) Assignee: Duquesne University of the Holy Ghost, Pittsburgh, PA (US)

(*) Notice: Subject to any disclaimer, the term of this patent is extended or adjusted under 35 U.S.C. 154(b) by 41 days.

(21) Appl. No.: 09/982,351

(22) Filed: Oct. 18, 2001

(65) Prior Publication Data

US 2003/0181467 A1 Sep. 25, 2003

(51) Int. Cl.[7] .................. C07D 487/04; C07D 491/048; A61K 31/519; A61P 35/00; A61P 35/04
(52) U.S. Cl. ..................... 514/265.1; 544/278; 544/280
(58) Field of Search ........................ 514/265.1; 544/280

(56) References Cited

U.S. PATENT DOCUMENTS

| | | | | | |
|---|---|---|---|---|---|
| 5,502,187 | A | * | 3/1996 | Ayer et al. .................... | 544/280 |
| 5,686,457 | A | * | 11/1997 | Traxler et al. ............... | 544/280 |
| 5,869,485 | A | * | 2/1999 | Missbach .................... | 544/280 |
| 5,939,420 | A | * | 8/1999 | Gangjee ....................... | 544/20 |
| 6,187,777 | B1 | * | 2/2001 | Norman et al. ............. | 544/280 |
| 6,462,060 | B2 | * | 10/2002 | Chong et al. ............... | 514/362 |
| 6,562,969 | B1 | * | 5/2003 | Robertus .................... | 544/260 |
| 2003/0114467 | A1 | * | 6/2003 | Shakespeare et al. ....... | 544/280 |

OTHER PUBLICATIONS

Jun, Bulletin of the Korean Chemical Society 17(8), 676–678 (1996).*
John A. Secrist et al, J. Organic Chem. 43(20) pp 3937–3941.*
Taylor, Heterocycles 36(8), 1897–1908 (1993).*
Benghiat, J. Pharmaceutical Sciences 75(2), 142–145 (1986).*
Kolata, "Two Drugs Eradicate Tumors in Mice" New York Times May 3, 1998, http://www.shamema.com/cancer-c.htm downloaded from the Internet Mar. 28, 2003.*
Marshall, "Setbacks for Endostatin" Science 295, 2198–2199 (Feb. 2002).*
"Learning for Angiogenesis Trial Failures" http://www.genomics.org.cn:8080/bgi/english/news/englishnews%20020320-4.htm downloaded from the Internet Mar. 26, 2003.*
Sweeney et al, Trends in Molecular Medicine vol. 9(1), Jan. 2003, pp. 24–29.*
Farkas, Biochimica et Biophysica Acta 781(102) 64–75 (1984).*
Receptor Tyrosine Kinases (RTKs) chart from http://www.kinase.com/mammalian/rtks.pdf.*
Cherrington et al., "New Paradigms for the Treatment of Cancer: The Role of Anti-Angiogenesis Agents", Advances in Cancer Research, 2000, pp. 1–38.

(List continued on next page.)

Primary Examiner—Mark L. Berch
(74) Attorney, Agent, or Firm—Debra Z. Anderson; Eckert Seamans Cherin & Mellott, LLC

(57) ABSTRACT

This invention discloses pyrrolo pyrimidine compounds, and pharmaceutically acceptable salts, solvates and prodrugs thereof, of the following formula (3):

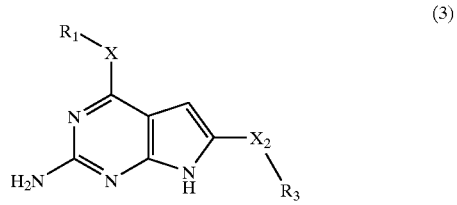

(3)

These compounds are useful in therapeutically and/or prophylactically treating patients with cancer by inhibiting receptor tyrosine kinases and/or dihydrofolate reductase and/or thymidylate synthase. Methods of using these compounds, are also disclosed.

15 Claims, 4 Drawing Sheets

OTHER PUBLICATIONS

Traxler et al., "Strategies toward the Design of Novel and Selective Protein Tyrosine Kinase Inhibitors", Pharmacol. Ther. vol. 82, Nos. 2–3, pp. 195–206, 1999.

Sun et al., "Inhibition of tumor angiogenesis by synthetic receptor tyrosine kinase inhibitors", Reviews, DDT vol. vol. 5 No. 8 Aug. 2000, pp. 344–353.

* cited by examiner

Target compounds:

1a: R = H; X = CH
1b: R = p-OMe; X = CH
1c: R = o-Cl; X = CH
1d: R = H; X = N
1e: R = 2',3'-C4H4; X = CH
1f: R = 3',4'-C4H4; X = CH

Synthetic Scheme:

MULTIPLE ACTING ANTI-ANGIOGENIC AND CYTOTOXIC COMPOUNDS AND METHODS FOR USING THE SAME

GOVERNMENT CONTRACT

This work was supported in part by the National Institutes of Health, U.S. Department of Health and Human Services under Contract Nos. R01 AI44661-03 and R01 CA89300-01. The Government may have certain rights in this invention.

FIELD OF THE INVENTION

This invention relates to pyrimidine compounds and pharmaceutically acceptable salts, solvates and prodrugs thereof. The present compounds have been found useful as antitumor and antiangiogenic agents. Methods using these compounds are also provided.

BACKGROUND OF THE INVENTION

Angiogenesis, the formation of new blood vessels, occurs during development and in normal adults during wound healing, pregnancy, and corpus luteum formation. Although angiogenesis is limited in normal adults, it is induced in many disease states including cancer, diabetic retinopathy, rheumatoid arthritis, psoriasis, atherosclerosis, and restenosis (reviewed in Folkman, 1995).

Tumors require angiogenesis to grow beyond 1–2 mm$^3$. (Folkman, 1990). The increased blood flow to the tumor allows for continued growth as well as metastasis because successful metastasis requires the presence of blood vessels to allow for the tumor cells to enter the circulation. The close interplay between angiogenesis and metastasis contributes to the poor prognosis seen in patients with highly angiogenic tumors. Cherrington et al., 2000.

Some of the most well characterized regulators of angiogenesis are growth factors and receptor tyrosine kinases (RTKs) involved in the migration and proliferation of endothelial cells. Of primary interest for angiogenesis are Flt-1 and Flk-1/KDR, the receptors for vascular endothelial growth factor (VEGF), as well as Tie 1 and Tie 2/Tek, the receptors for angiopoietins. These four receptors are expressed primarily on endothelial cells and play a direct role in angiogenesis. Additional RTKs with broader expression patterns implicated in angiogenesis are platelet-derived growth factor receptors (PDGFRs); fibroblast growth factor receptors (FGFRs); the hepatocyte growth factor/scatter factor (HGF/SF) receptor, Met; and epidermal growth factor receptors (EGFRs), although it is thought that the EGFR is likely to act predominantly in directly driving the growth of tumor cells rather than through angiogenesis. Cherington et al., 2000.

VEGF is a dimeric protein also known as vascular permeability factor because it acts on endothelial cells to regulate permeability of those cells as well as their proliferation. These two activities are mediated through its tyrosine kinase receptors, VEGFR1/Flt-1 and VEGFR2/Flk-1/KDR (KDR is the human homologue of Flk-1). VEGF and its receptors are expressed in angiogenic tissues during development, wound healing and other situations when angiogenesis occurs. The role of VEGF in tumor angiogenesis has also been clearly demonstrated using tumor models in rodents (reviewed in Hanahan, 1997; Shawver et al., 1997); there is an extensive literature exists linking VEGF with human cancers such as pulmonary adenocarcinoma (Takanami et al., 1997) and non-small cell carcinoma (NSCLC) (Fontanini et al., 1999; Takahama et al., 1998; Ohta et al., 1996). Survival of patients with VEGF-positive tumors was significantly less than patients with VEGF-negative tumors. For example, in one study of non-small cell carcinoma (NSCLC), patients with low VEGF levels had a median survival time of 151 months, whereas those with high VEGF expression had a mean survival time of only 8 months. Ohta et al., 1996.

VEGF and its receptors, in particular, serve as excellent targets for anti-angiogenesis therapy because KDR is an endothelial cell-specific VEGF receptor expressed primarily during the angiogenic process. The VEGF signaling cascade has been validated as a target for therapeutic intervention by several methods. See, e.g., Saleh et al., 1996, Claffey et al., 1996, Kim et al., 1993 and Asano et al., 1995.

Epidermal growth factor (EGF) is one of several naturally occurring proteins that promotes normal cell proliferation in a tightly regulated manner by binding to its receptor, EGFR, and sending growth signals via the receptor tyrosine kinase enzyme activity to the nucleus of the cell and thus controlling growth. In many human cancers, EGFR is either overexpressed or mutated, leading to aberrant signaling and the development of a tumor; thus inhibition of EGF receptor kinase is also a target in anti-tumor therapy.

Many pyrimidine systems have been studied for their ability to inhibit growth of tumors, through inhibition of angiogenesis and/or inhibition of cell growth, by targeting receptor tyrosine kinases. See, for example, Sun, Li and McMahon, G. "Inhibition of tumor angiogenesis by Synthetic Receptor Tyrosine Kinase Inhibitors". *Drug Discov Today* 2000, 5 (8): 344–353, and Traxler, P. and Furet, P., "Strategies toward the Design of Novel and Selective Protein Tyrosine Kinase Inhibitors" *Pharmacol. Ther.* 1999 82 (2–3): 195–206, which disclose synthetic pyrimidine compounds which have been shown to be effective TK inhibitors.

Pyrimidine systems have also been shown to inhibit dihydrofolate reductase (DHFR) enzyme activity. Because DHFR reduces dihydrofolate to tetrahydrofolate, inhibition of DHFR deprives the cell of tetrahydrofolate, without which the cell cannot produce 5,10-methylene-tetrahydrofolate, essential for cell growth. The inhibition of DHFR results in the inhibition of DNA synthesis and leads to cell death.

Additionally, some pyrimidine derivatives are known to function as thymidylate synthase (TS) inhibitors. TS, along with DHFR, forms part of the system responsible for the synthesis of deoxythymidylate (dTMP) from deoxyuridylate (dUMP). TS catalyzes the sole de novo synthesis of dTMP from dUMP. Inhibition of TS, therefore, deprives the cell of thymidine, which is an essential constituent of DNA.

In general, it is highly desirable to develop new antiangiogenic compounds which inhibit formation of new blood vessels and development of a new blood supply, as these can selectively target various tumor types and prevent growth of circulation in the tumor and inhibit metastasis. Because angiogenesis is limited in healthy adults, compounds which inhibit angiogenesis can selectively target tumors as compared with other compounds and anti-cancer agents using other modes of action, which often indiscriminately act on tumor and healthy cells alike. There is a need for compounds which provide the desired enzyme inhibition with a high degree of selectivity and low toxicity.

SUMMARY OF THE INVENTION

The present invention provides pyrimidine compounds, and pharmaceutically acceptable salts, solvates and prodrugs thereof, having the formula (1):

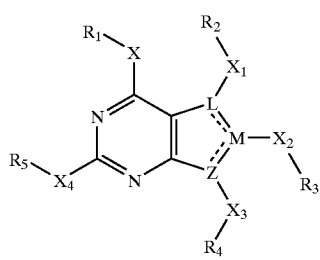

(1)

where X, $X_1$, $X_2$, $X_3$ and $X_4$ are from one to about three atoms, are the same or different and are independently selected from the group consisting of hydrogen, an alkyl group, a alkenyl group, an heteroalkyl group and an heteroalkenyl group, and any carbons or nitrogens of said alkyl group, alkenyl group, heteroalkyl group or heteroalkenyl group can optionally be substituted with a straight, branched or cyclic lower alkyl group of from 1 to about 6 carbons;

Z is selected from the group consisting of C, CH, $CH_2$, N, NH, S, O, CH=CH, CH=N and N=CH;

L is selected from the group consisting of C, CH, $CH_2$, N, NH, S, O, CH=CH, CH=N and N=CH, but when Z is C, CH, CH=CH or $CH_2$ then L is N, NH, S or O;

M is selected from the group consisting of carbon and CH;

the chemical bond between L and M is selected from the group consisting of a single bond and a double bond, and M is carbon when the bond is a double bond, and M is CH when the bond is a single bond;

the chemical bond between M and Z is selected from the group consisting of a single bond and a double bond, and M is carbon when the bond is a double bond, and M is CH when the bond is a single bond;

but when the bond between L and M is a double bond the bond between M and Z is a single bond;

at least one of $R_2$, $R_3$, $R_4$, or $R_5$ is present;

$R_1$, $R_4$ and $R_5$ are the same or different and are selected from the group consisting of hydrogen, an alicyclic group, a heterocyclic group, an aryl group, a heteroaryl group, an alkylaryl group, a alkylheteroaryl group, a substituted aryl group, a substituted heteroaryl group, a substituted alkylaryl group and a substituted alkylheteroaryl group;

$R_2$ and $R_4$ are optional, are the same or different and are selected from the group consisting of hydrogen, an alicyclic group, a heterocyclic group, an aryl group, a heteroaryl group, an alkylaryl group, a alkylheteroaryl group, a substituted aryl group, a substituted heteroaryl group, a substituted alkylaryl group, a substituted alkylheteroaryl group, and p-aroyl-glutamate;

and each substituent of any substituted group is the same or different and is selected from the group consisting of a straight, branched or cyclic lower alkyl, alkenyl or alkynl group of from one to about 6 carbons, an group, an alkoxyaryloxy group, and a halogen.

In one aspect of the present invention, these pyrimidine compounds can function as receptor tyrosine kinase inhibitors, and prevent the development of new blood vessels in tumors. Specifically, these compounds have been found to inhibit several receptor tyrosine kinases, including vascular endothelial growth factor (VEGF), epidermal growth factor (EGF) and platelet derived growth factor (PDGF) receptor tyrosine kinases. Thus, the compounds of the present invention are dual acting in that they can inhibit angiogenesis by inhibiting tyrosine kinases directly involved in angiogenesis, (such as by inhibiting the VEGF receptor tyrosine kinase), and inhibit receptor tyrosine kinases involved in cell growth, for example, by competitively binding to TK receptors such as the EGF receptor tyrosine kinase. These compounds have an antiangiogenic and an antitumor effect.

In an additional aspect of the present invention, certain of these pyrimidine compounds function as triple or quadruple acting agents. That is, they inhibit receptor tyrosine kinases, and they also inhibit DHFR and/or thymidylate synthase, thus further providing additional inhibition of tumor growth. Both the dual, triple and quadruple acting compounds are unique in their ability to provide multiple mechanisms of action in structurally distinct compounds. None of the existing compounds known to inhibit receptor tyrosine kinases are known to additionally inhibit DHFR and/or TS, nor do any have the distinct chemical structures described and claimed herein. It is thought that the compounds having less bulky substituents at the 4-position on the pyrimidine ring are able to provide the multiple mechanisms of action, although the inventor does not wish to be bound by this.

Methods for using these compounds in the treatment of various illnesses are also within the scope of the invention; for example, these compounds are useful for therapeutic and/or prophylactic purposes as antitumor or anti-angiogenic agents or to otherwise destroy or minimize growth or proliferation of cancerous cells in cancer patients or in the treatment of other illnesses.

It is an object of the present invention, therefore, to provide pyrimidine derivative compounds, and pharmaceutically acceptable salts and prodrugs thereof, having antitumor and/or anti-angiogenic activity.

It is an additional object of the present invention to provide pyrimidine compounds, and pharmaceutically acceptable salts and prodrugs thereof, for substantially inhibiting receptor tyrosine kinase(s) activity.

It is a further object of this invention to provide pyrimidine compounds, and pharmaceutically acceptable salts and prodrugs thereof, for substantially inhibiting receptor tyrosine kinases and/or dihydrofolate reductase and/or thymidylate synthase enzymes.

It is an additional object of this invention to provide a method of the present pyrimidine compounds and their derivatives to treat various illnesses such as cancer.

These and other aspects of the invention will be more fully understood from the following detailed description of the invention, the drawings and the claims appended hereto.

BRIEF DESCRIPTION OF THE DRAWINGS

The invention is further illustrated by the following non-limited figures in which.

DETAILED DESCRIPTION OF THE INVENTION

Figure 1:
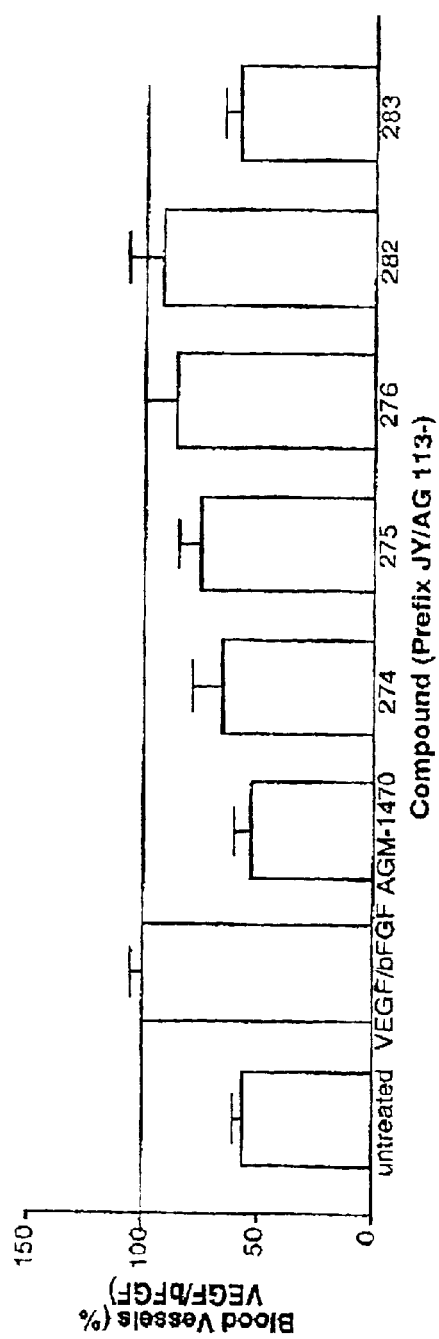
FIG. 1 shows the results of the CAM assay procedure.
Figure 2:
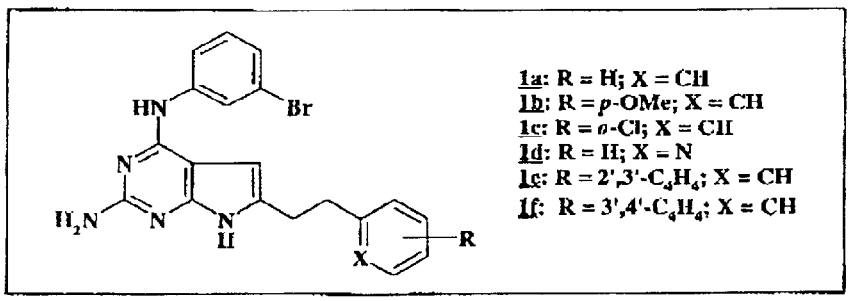
FIG. 2 shows a schematic diagram of methods of preparing the 2-amino 6-substitute pyrrolo[2,3-d]pyrimidines of the present invention.
Figure 2:
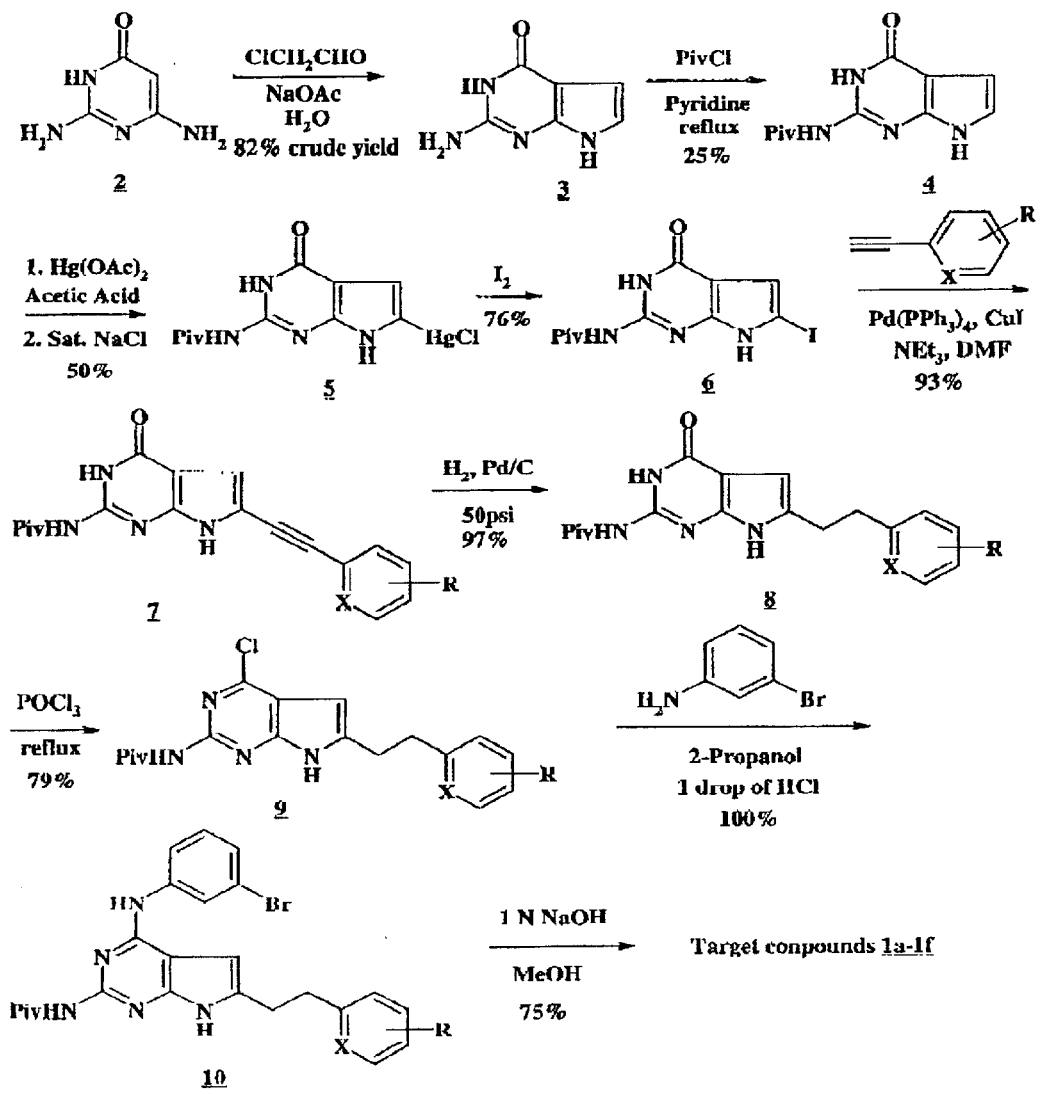
Figure 3:
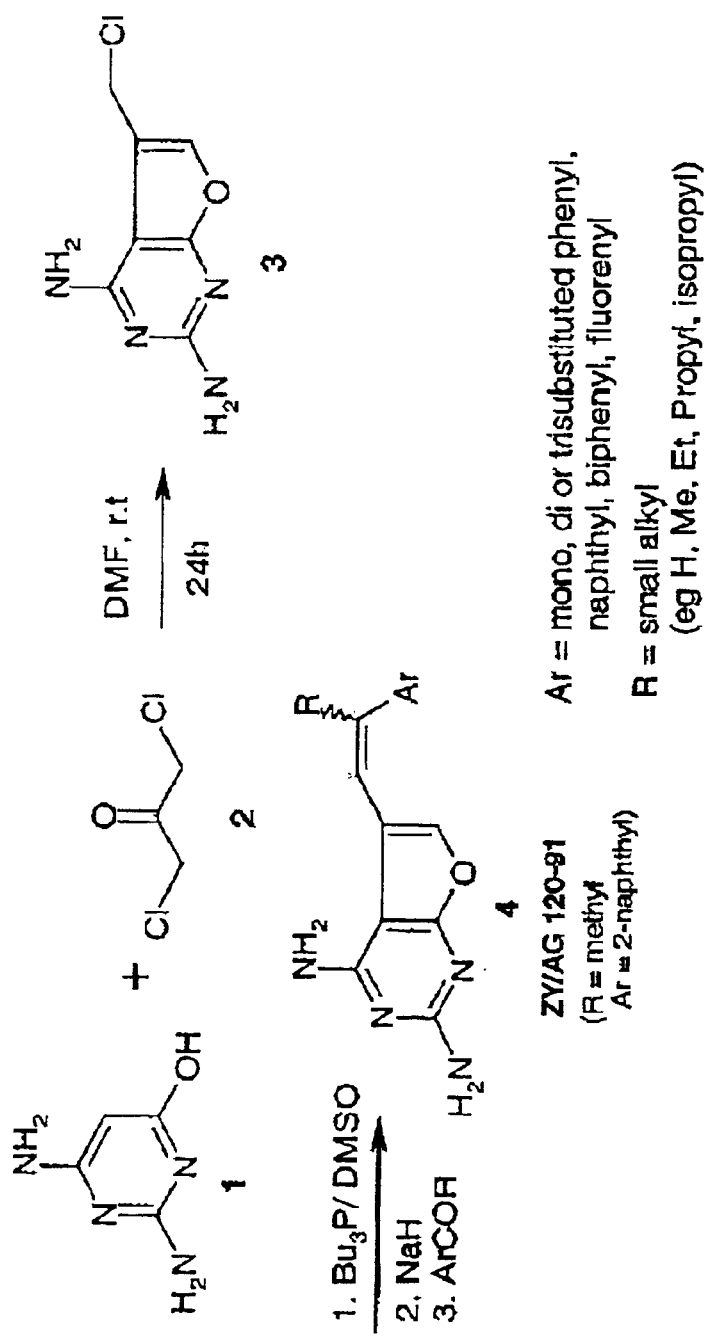
FIG. 3 shows a schematic diagram of the methods of preparing 2,4-diamino 5-substituted furo[2,3-d]pyrimidines.

The present invention is directed to compounds, and pharmaceutically acceptable salts, solvates, and prodrugs thereof, having formula (1):

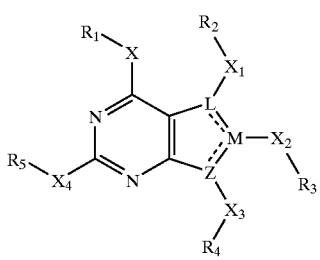

(1)

where X, $X_1$, $X_2$, $X_3$ and $X_4$ are from one to about three atoms, are the same or different and are independently selected from the group consisting of hydrogen, an alkyl group, an alkenyl group, a heteroalkyl group and a heteroalkenyl group, and any carbons or nitrogens of said alkyl group, alkenyl group, heteroalkyl group or heteroalkenyl group can optionally be substituted with a straight, branched or cyclic lower alkyl group of from 1 to about 6 carbons;

Z is selected from the group consisting of C, CH, $CH_2$, N, NH, S, O, CH=CH, CH=N and N=CH;

L is selected from the group consisting of C, CH, $CH_2$, N, NH, S, O, CH=CH, CH=N and N=CH, but when Z is C, CH, CH=CH or $CH_2$ then L is N, NH, S or O;

M is selected from the group consisting of carbon and CH;

the chemical bond between L and M is selected from the group consisting of a single bond and a double bond, and M is carbon when the bond is a double bond, and M is CH when the bond is a single bond;

the chemical bond between M and Z is selected from the group consisting of a single bond and a double bond, and M is carbon when the bond is a double bond, and M is CH when the bond is a single bond;

but when the bond between L and M is a double bond the bond between M and Z is a single bond;

at least one of $R_1$, $R_2$, $R_3$, $R_4$, or $R_5$ is present;

$R_1$, $R_4$ and $R_5$ are the same or different and are selected from the group consisting of hydrogen, an alicyclic group, a heterocyclic group, an aryl group, a heteroaryl group, an alkylaryl group, a alkylheteroaryl group, a substituted aryl group, a substituted heteroaryl group, a substituted alkylaryl group and a substituted alkylheteroaryl group;

$R_2$ and $R_3$ are the same or different and are selected from group consisting of hydrogen, an alicyclic group, a heterocyclic group, an aryl group, a heteroaryl group, an alkylaryl group, a alkylheteroaryl group, a substituted aryl group, a substituted heteroaryl group, a substituted alkylaryl group, a substituted alkylheteroaryl group, and p-aroyl-glutamate;

and each substituent of any substituted group is the same or different and is selected from the group consisting of a straight, branched or cyclic lower alkyl, alkenyl or alkynl group of from one to about 6 carbons, an alkoxy group, an alkoxyaryloxy group, and a halogen.

As used herein, the term "lower alkyl" group refers to those lower alkyl groups having one to about six carbon atoms, such as for example methyl, ethyl, propyl, butyl, pentyl, hexyl, cyclopropyl, cyclobutyl, cyclohexyl, cyclopropylmethyl or cyclobutylmethyl groups. Alkyl groups sharing one to about six carbon atoms are preferred. These lower alkyl groups are straight chain, branched chain or cyclic (alicyclic hydrocarbon) arrangements. The carbon atoms of these straight chain, branched chain or cyclic arranged alkyl groups may have one or more substituents for the hydrogens attached to the carbon atoms.

As used herein, the terms "heteroalkyl" and "heteroalkenyl" will be used to refer to alkyl or alkene chains from one to about 3 atoms where one or more of the carbons has been replaced with nitrogen, oxygen or sulfur. Thus "heteroalkyl" and "heteroalkenyl" groups will include, for example, C—C—N, C—S, S—C, C—O, C—C—O, O—C, N—C—C, N—C=C and other various combinations, as will be apparent to one skilled in the art. The above list is not meant to be exhaustive, and many combinations are contemplated as within the scope of the present invention.

"Aryl" groups, as used herein, will refer to compounds whose molecules have an aromatic ring structure, such as the six-carbon ring of benzene, or multiple rings which are either fused or unfused, such as condensed six-carbon rings of other aromatic derivatives. The term "aryl" is also defined to include diaryl, triaryl and polyaryl groups, which would have two, three or more rings, respectively. Thus, suitable aryl groups would include, for example, phenyl, biphenyl, naphthyl, phenanthrene, anthracene groups and aryl oxyaryl groups. This list is not meant to be exhaustive, and any aryl group, as these terms are defined above and commonly understood in the art, are within the scope of the present invention.

The term "heteroaryl", as used herein, will be used to refer to aromatic ring structures having at least one atom in the ring which is not carbon, such as oxygen, nitrogen or sulfur. "Heteroaryls" as used herein also refers to aromatic ring structures that are part of larger ring structures, such as two or three member ring systems, which may be fused or unfused, in which one of the rings is as described above. Thus, "heteroaryl" can refer to ring systems in which one or more rings contain a heteroatom and one or more rings do not. It will be understood that this list is not meant to be exhaustive, and that any heteroaryl group, as these terms are defined above and commonly understood in the art, are within the scope of the present invention. Examples include but are not limited to pyrroles, thiophenes, furans, imidazoles, and the like, as well as fused ring structures having rings of different sizes, such as benzofurans, indoles, purines, and the like.

Also included within the scope of the present invention are alicyclic groups, as that term is understood in the art, and heterocyclic groups. As used herein, the term "heterocyclic group" will refer to non-aromatic cyclic substituents in which one or more members of the ring is not carbon, for example oxygen, sulfur or nitrogen.

The terms "alkylaryl" (or "alkaryl") or "alkylheteroaryl" as used herein will refer to groups having an alkyl moiety attached to an aryl or heteroaryl ring. The alkyl moiety is preferably a straight, branched or cyclic alkyl group having one to about six carbon atoms. This alkyl moiety may also contain oxygen, nitrogen or sulfur atoms, and can therefore be an alkoxy group. The aryl or heteroaryl moiety of the alkylaryl group is a substituted or unsubstituted aryl or heteroaryl group, as these terms are described above. As used herein, the terms "alkylaryl" or "alkylheteroaryl" will also be used to refer to arylalkyl groups or heteroarylalkyl groups, as those terms are understood in the art, and will denote attachment of such a substituent at either the alkyl or the aryl portion of the group. Thus, for example, a benzyl group would be embraced by the term "alkylaryl".

Any of the cyclic substituents described above, such as the aryl, heteroaryl, alkylaryl, alkylheteroaryl, alicyclic, or heterocyclic groups are optionally substituted with one or more substituents as listed above. In the case of more than one substituent, the substituents are independently selected. "Alkoxy groups" and "alkyl groups" include straight or branched chains having up to about six members. "Halogen" refers to chlorine, bromine, iodine and fluorine. "Aryl and heteroaryl groups" are as described above. When a carboxylic acid is a substituent, it will be appreciated that the moiety represents an acid such as benzoic acid. "Acyl" refers to an organic acid group in which the OH is replaced by some other substituent, and is generally designated as RCO— where R is a $C_{1-6}$ alkyl, $C_{2-6}$ alkenyl, or $C_{2-6}$ alkynyl straight or branched chain group.

As used herein, the terms "aroyl" or "heteroaroyl", such as when used within the term p-aroyl-L-glutamate, refers to benzoyl, napthoyl, thiophenoyl, furophenoyl, pyrroyl, and any other "aroyl" or "heteroaroyl" as these terms would be understood by one skilled in the art. "Aroyl" and "heteroaroyl" are generally defined in the art as an aromatic or heteroaromatic compound having a carbonyl moiety. "Glutamate" will be understood as representing both the ester form (glutamate) and the acid form (glutamic acid).

It will appreciated by those skilled in the art that a general formula depicting compounds having side chains with adjacent carbons having a double bond will result in both cis and trans isomers as possible structures. Both the cis and trans isomers, and mixtures thereof, of any such compound within the broad general formula described in formulas (1), (2) and (3) are contemplated as being within the present invention.

Compounds of the above general formula (1) have been found to inhibit many receptor tyrosine kinases such as VEGF, EGF and other receptor tyrosine kinases and are thus dual-acting compounds; that is, they exert an anti-cancer effect by inhibiting both angiogenesis and cell growth and proliferation.

In an additional aspect of the present invention, certain compounds of the above general formula have been found to exert an additional anti-cancer effect by inhibiting dihydrofolate reductase and/or thymidylate synthase, in addition to their inhibition of receptor tyrosine kinases. These compounds are thus triple- or quadruple-acting anti-cancer agents in that they provide anti-tumor activity in multiple, distinct ways. As described above, it is thought that compounds of the above general formula (1) having less bulky substituents in the 4-position on the pyrimidine ring are able to function as receptor tyrosine kinase, DHFR and/or TS inhibitors, although the inventor does not wish to be bound by this.

In preferred embodiments, compounds of the present invention will have the general formula (2):

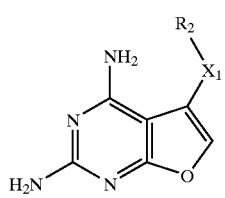

(2)

where $X_1$ is

and $R_6$ is selected from the group consisting of hydrogen and a straight, branched or cyclic lower alkyl group of from 1 to about 6 carbons;

$R_2$ is selected from the group consisting of hydrogen, an alicyclic group, a heterocyclic group, an aryl group, a heteroaryl group, an alkylaryl group, a alkylheteroaryl group, a substituted aryl group, a substituted heteroaryl group, a substituted alkylaryl group, a substituted alkylheteroaryl group, and p-aroyl-glutamate;

and each substituent of any substituted group is the same or different and is selected from the group consisting of a straight, branched or cyclic lower alkyl, alkenyl or alkynl group of from one to about 6 carbons, an alkoxy group, an alkoxyaryloxy group, and a halogen.

In additional preferred embodiments, compounds of the present invention will be represented as having the general formula (3):

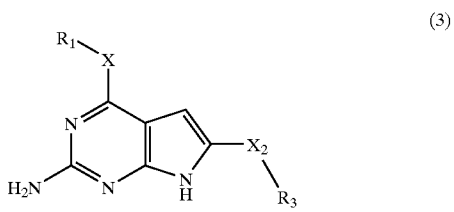

(3)

where X and $X_2$ are from one to about three atoms, are the same or different and are independently selected from the group consisting of hydrogen, an alkyl group, an alkenyl group, a heteroalkyl group and a heteroalkenyl group, and any carbons or nitrogens of said alkyl group, alkenyl group, heteroalkyl group or heteroalkenyl group can optionally be substituted with a straight, branched or cyclic lower alkyl group of from 1 to about 6 carbons;

at least one of $R_1$ or $R_3$ are present;

$R_1$ is selected from the group consisting of hydrogen, an alicyclic group, a heterocyclic group, an aryl group, a heteroaryl group, an alkylaryl group, a alkylheteroaryl group, a substituted aryl group, a substituted heteroaryl group, a substituted alkylaryl group and a substituted alkylheteroaryl group;

$R_3$ is selected from the group consisting of hydrogen, an alicyclic group, a heterocyclic group, an aryl group, a heteroaryl group, an alkylaryl group, a alkylheteroaryl group, a substituted aryl group, a substituted heteroaryl group, a substituted alkylaryl group, a substituted alkylheteroaryl group, and p-aroyl-glutamate;

and each substituent of any substituted group is the same or different and is selected from the group consisting of a straight, branched or cyclic lower alkyl, alkenyl or alkynl group of from one to about 6 carbons, an alkoxy group, an alkoxyaryloxy group, and a halogen.

As used herein, the term "pharmaceutically acceptable salts and solvates" include salts or solvates of the present pyrimidine compounds suitable for use in pharmaceutical applications. One skilled in the art would easily be able to determine whether a salt or solvate form of any given compound is suitable for use as a pharmaceutical. Examples of pharmaceutically acceptable salts include but are not limited to, acetate, formate, glucuronate, ethantate, and sulfonate. Other examples include alkaline metal, alkaline earth metal, other non-toxic metals, ammonium and substituted ammonium salts such as the sodium, potassium, lithium, calcium, magnesium, aluminum, zinc, ammonium, trimethyl ammonium, triethyl ammonium, tetrabutyl ammonium, pyridinium and substituted pyridinium salts. "Pharmaceutically acceptable prodrugs" similarly refers to any prodrug formulations of the present compounds. A prodrug will be understood by those skilled in the art as a chemical compound that is converted into an active curative agent by processes within the body. Other formulations comprising the pyrimidine compounds described herein are also within the scope of the present invention. Salts, solvates and prodrugs of the compounds of Formula 1, 2 or 3 can be made by standard methods well known to those skilled in the art.

The present invention further relates to methods of using the above-described compounds, and pharmaceutically acceptable salts and prodrugs thereof, to treat a patient with an illness. "Treating" and "treatment" are used generically throughout to refer to both therapeutic and prophylactic treating/treatment that is effected by inhibition of receptor tyrosine kinases (referred to generally as "receptor tyrosine kinase"), and of DHFR and/or thymidylate synthate. As used herein, the term "illness" refers to various types of cancer including, but not limited to, leukemia, lung cancer, colon cancer, CNS cancer, melanoma, ovarian cancer, renal cancer, prostate cancer, breast cancer, and various other illnesses such as diabetic retinopathy, rheumatoid arthritis, psoriasis, atherosclerosis, and restenosis.

A method of treating a patient for an illness according to the present invention comprises administering an effective amount of one or more compounds of Formula 1, 2 or 3 to a patient.

As used herein, the term "patient" means adult members of the animal kingdom, including, but not limited to, human beings.

As used herein, the term "effective amount" refers to that amount of any of the present compounds required to bring about a desired effect in a patient. The desired effect will vary depending on the illness being treated. For example, the desired effect may be reducing tumor size, destroying cancerous cells, preventing metastasis or reducing symptoms associated with the various other diseases listed above and contemplated as being within the treatment methods of the present invention. On its most basic level, an effective amount is that amount needed to inhibit the receptor tyrosine kinase(s) generally and/or DHFR and/or thymidylate synthate. Any amount of inhibition will yield a benefit to a patient and is therefore within the scope of the invention.

It will be appreciated that the effective amount will vary from patient to patient depending on such factors as the illness being treated, the severity of the illness, the size of the patient being treated, the patient's ability to mount an immune response, and the like. The determination of an effective amount for a given patient is within the skill of one practicing in the art. Typically an effective amount will be determined by evaluating potency in standard ex vivo cellular systems, followed by preclinical and clinical in vivo assessment.

Administration can be by any means known in the art, such as parenterally, orally or topically. The pyrimidine compound can be contained within a suitable pharmaceutical carrier for administration according to the present methods. "Suitable pharmaceutical carrier" refers to any pharmaceutical carrier known in the art that will solubilize the present compounds and will not give rise to compatibility problems and includes any and all solvents, dispersion media, coatings, antibacterial and antifungal agents, isotonic and absorption delaying agents, and the like. The use of such media and agents for pharmaceutical use is well known in the art. Use of any of these media or agents is contemplated by the present invention, absent compatibility problems with the chimeric proteins. Preferred carriers include physiologic saline and 5% dextrose.

It is especially advantageous to formulate parenteral compositions in dosage unit form for ease of administration and uniformity of dosage. Dosage unit form as used herein refers to physically discrete units suited as unitary dosages for the patients being treated, each unit containing a predetermined quantity or effective amount of pyrimidine compound to produce the desired effect in association with the pharmaceutical carrier. The specification for the dosage unit forms of the invention are dictated by and directly dependent on the particular compound and the particular effect to be achieved.

EXAMPLES

The following examples are intended to illustrate the invention, and should not be construed as limiting the invention in any way. Standard test procedures familiar to those skilled in the art were used in the examples, such as those procedures described by Gangjee, A., et al., in "Effect of bridge region variation on antifolate and antitumor activity of classical 5-substituted 2,4-diaminofuro[2,3-d]pyrimidines", *J. Med. Chem.*, Vol. 38, pp. 3798–3805 (1995); and "Novel 2,4-diamino-5-substituted-pyrrolo[2,3-d]pyrimidines As Classical and Non-Classical Antifolate Inhibitors of Dihydrofolate Reductases", *J. Med. Chem.*, Vol. 38, pp. 2158–2165 (Jun. 6, 1995) and references disclosed therein, as well as *Angiogenesis Protocols*, J. Clifford Murray ed., Humana Press, 2001.

Example 1

CAM Assay Procedure

Human VEGF-165 and BFGF (200 ng each) were added to saturation to a microbial testing disk and placed onto the chorioallantoic membrane (CAM) of 10-day old chicken embryos. Eight hours after the growth factor treatment, unknown compounds (100 µg) were added to the same microbial testing disk. Growth factors and embryos were allowed to incubate an additional 40 hours. CAMS were removed, paraformaldehyde (4% in PBS) fixed, placed onto Petri dishes, and digital images taken at 7.5× using a dissecting microscope. A 1×1-cm grid was then added to the digital CAM images and the number of vessels within each grid counted as a measure of vascularity. In all studies, AGM-1470, a known potent anti-angiogenic agent, was used as a positive control for each experiment at a dose of 10 ng/embryo. Data were then graphed (FIG. 1) as a percent of growth factor-induced blood vessel amounts. As can be seen in FIG. 1, compounds JY/AG 113-274 and JY/AG 113-283 provided inhibition almost as effective as that of AGM-1470.

Example 2

Synthesis of the 2,4-Diamino-5(2-alkyl,2-aryl)vinylfuro[2,3-d]pyrimidines

To a solution of 2,4-diamino-5-(chloromethyl)furo[2,3-d]pyrimidine, 3, (1.0 g, 5 mmol) in anhydrous DMSO (15 mL) was added tributylphosphine (92%, 1.7 g 7.5 mmol), and the resulting mixture was stirred at 60° C. in an oil bath for 3 hrs. under $N_2$ to form the phosphonium salt. The deep orange solution was then cooled to room temperature. To this solution was added sodium hydride (90% dispersion in mineral oil, 0.2 g, 6 mmol), followed by the desired commercially available aryl alkyl ketone (5.5 mmol). The reaction mixture was stirred at room temperature for 24–32 h.

TLC showed the disappearance of the starting 2,4-diamino-5-(chloromethyl)furo[2,3-d]pyrimidine and the formation of two (olefinic) spots. The reaction was quenched with 20 mL methanol, washed with two portions of 50 mL methanol, and the resulting solution was evaporated under reduced pressure to dryness. To the residue was added 6 g of silica gel and $CHCl_3$ (25 mL) and the slurry was loaded onto 4×20 cm dry silica gel column and flash chromatographed initially with $CHCl_3$ (300 mL), then sequentially with 2% MeOH in $CHCl_3$ (250 mL); 5% $CH_3OH$ in $CHCl_3$ (300 mL) and 10% $CH_3OH$ in $CHCl_3$ (250 mL). Fractions that showed the desired spot on TLC were pooled and evaporated to dryness and the residue was recrystallized from ethylacetate to afford the desired olefinic targets.

Example 3

Synthesis of E/Z-2,4-Diamino-5(2-methyl,2-2'-naphthyl)-vinylfuro[2,3-d]pyrimidine Compound 3 (1.0 g, 5 mmol) and 2'-acetonaphthone (940 mg, 5.5 mmol) 28 h afforded 21 (480 mg, 30%) as yellow needles: mp 238.2–247.5° C.; $R_f$=0.55 and 0.52 ($CH_3Cl$/$CH_3OH$ 5:1); $^1H$ NMR (DMSO-$d_6$) (E:Z=2.1) E-isomer δ2.34 (s, 3H, 9-$CH_3$), 6.09 (s, 2H, 4-$NH_2$), 6.52 (s, 2H, 2-$NH_2$), 7.05 (s, 1H, 8-CH), 7.551–7.49 (m, 3H, 6-CH and $C_{10}H_7$), 7.96–7.89 (m, 4H, $C_{10}H_7$), 8.09(s, 1H, $C_{10}H_7$); Z-isomer δ2.26 (s, 3H, 9-CH3), 5.99 (s, 2H, 4-$NH_2$), 6.29 (s, 1H, 8-CH), 6.54 (s, 2 H, 2-$NH_2$), 6.67 (s, 1H, 6-CH), 7.13–7.17 (m, 2H, $C_{10}H_7$), 7.70–7.89 (m, 4H, $C_{10}H_7$)Anal. ($C_{19}H_{16}N_4O$) C, H, N.

Example 4

Synthesis of (R,S) 2,4-Diamino-5(2-alkyl-2-arylethyl) furo [2,3-d]pyrimidines:

To a solution of the olefinic intermediate (0.3–0.7 mmol) in a mixture of $CHCl_3$ (50 mL) and $CH_3OH$ (15 mL) was added 5% palladium on activated carbon (0.20 g), and the suspension was hydrogenated in a Parr apparatus at room temperature and 40–55 psi for 3–24 h, TLC indicated the disappearance of the starting material and the formation of one major spot. The reaction mixture was filtered through Celite, washed with 30% $CH_3OH$ in $CHCl_3$ (3×20 mL). After evaporation of the solvent, $CH_3OH$ (50 mL) was added to afford a solution. To this solution was added 5 g silica gel and the mixture was evaporated under reduced pressure to dryness. The silica gel plug was loaded on a dry silica gel column (2×16 cm) and flash chromatographed initially with $CHCl_3$ (150 mL), then sequentially with 1% $CH_3OH$ in $CHCl_3$ (150 mL), 2% $CH_3OH$ in $CHCl_3$ (150 mL), and 5% $CH_3OH$ in $CHCl_3$ (150 mL). Fractions which showed the major spot on TLC were pooled and evaporated to dryness. The residue was recrystallized from $CH_3OH$ or other solvent combinations as indicated to afford the desired target compounds. The yields varied from 50–80%.

Example 5

(R,S) 2,4-Diamino-5(2'-naphethenylpropyl)furo[2,3-d] pyrimidine (37)

(100 mg, 0.3 mmol) 50 psi 5 h afforded 37 (50 mg, 50%) as white crystals: mp 230.2–232° C.; $R_f$=0.57 (EtOH/EtOAc/Hexane 1:2:1); $^1H$ NMR (DMSO-$d_6$) δ1.29–1.31 (d, 3H, 9-$CH_3$), 2.98–3.00 (d, 2H, 8-$CH_2$), 3.09–3.17 (m, 1H, 9-CH), 3.83 (s, 3 H, OMe), 5.99 (s, 2H, 4-$NH_2$), 6.39 (s, 2H, 2-$NH_2$), 6.88 (s, 1H, 6-CH), 7.08–7.11 (t,1H, $C_{10}H_7$), 7.24 (d, 1H, $C_{10}H_7$), 7.37–7.40 (d, 1H, $C_{10}H_7$), 7.61 (s, 1 H, $C_{10}H_7$) 7.69–7.76 (dd, 2H, $C_{10}H_7$). Anal. ($C_{19}H_{18}N_4O.0.1$ $H_2O$) C, H, N.

Example 6

Phospho-EGER and Phospho-Flk1 Expression

Figure 4A:
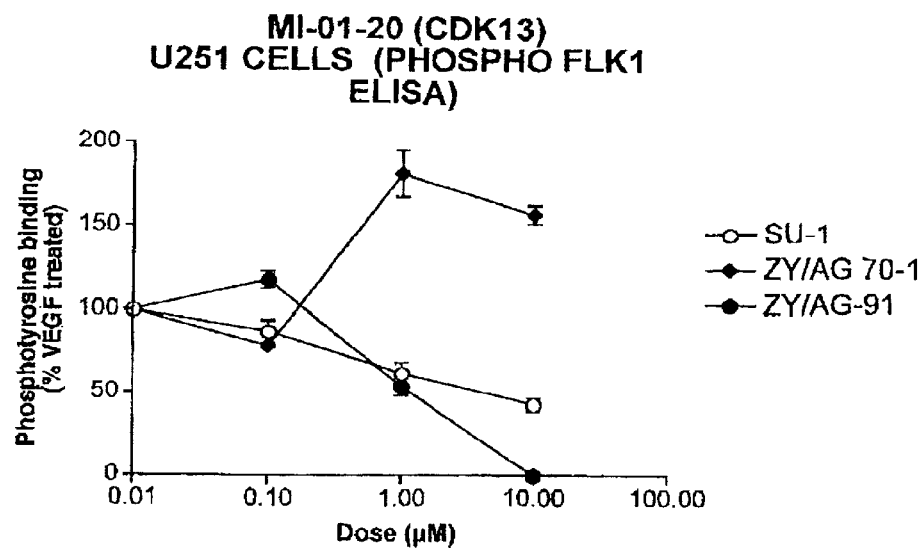
FIGS. 4a and 4b show results of the phospho-EGFR and phospho-Flk1 assay for the triple acting compounds.
Figure 4B:
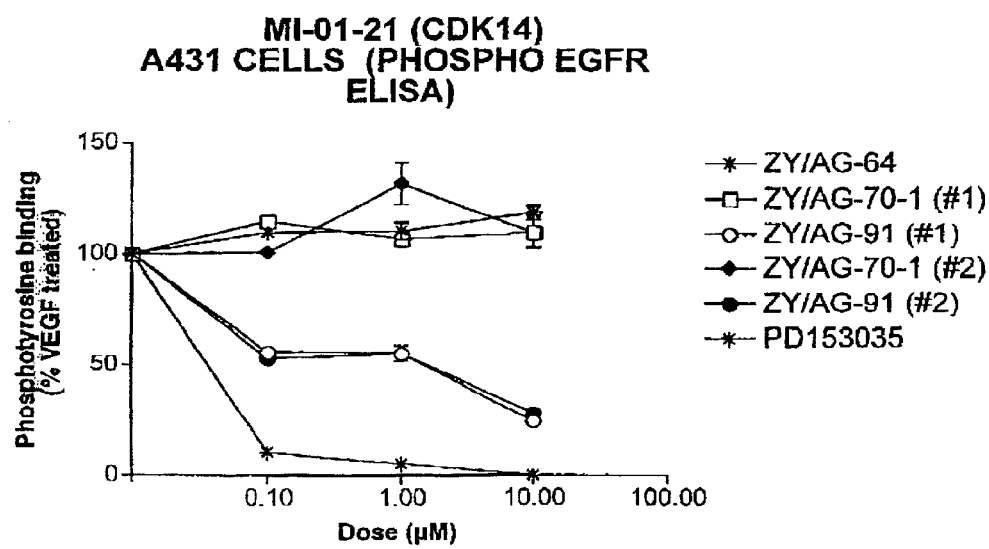

A phosphotyrosine ELISA or "cytoblot" on was used on whole cells to determine levels of RTK phosphorylation, as described in Stockwell et al. (Chem Biol 6(2) 71–83 (1999). A431 human epithelial carcinoma cells (overexpressing EGFR) and U2551 glioblastoma (known to overexpress Flk-1) were seeded at 50% confluence into 96-well plates. Cells were allowed to attach and grow overnight in opti-MEM low serum media (Gibco-BRL) to reduce background phosphorylation levels. Cells were then treated with anti-angiogenic compounds for one hour in incomplete medium and then EGF (50 ng/ml) or VEGF (100 ng/ml) was added for 30 minutes. Reactions were stopped by the aspiration of media and the addition of phosphate buffered saline (PBS) containing 0.05% triton X-100, protease inhibitor cocktail and phosphatase inhibitor cocktail 2 (Sigma Chemical company) for 10 minutes on ice. Cells were then fixed at 60° C. for 30 minutes and then cold methanol added to the cells for five minutes to further permeabilize them for antibody penetration. Cells were blocked for one hour with 1% bovine serum albumin in PBS, washed twice in PBS, and then anti-phosphotyrosine-HRP conjugate (Oncogene Research) added at 1:250 dilution overnight. The antibody was then removed, the cells washed three times in PBS with 1% BSA and once with PBS, and luminol-peroxide reagent added (Pierce Biochemical) for 5 minutes. Plates were read for chemilluminescence using a imaging system (ImageStation, Kodak-NEN) for 16×3 seconds and saved as a digitized image. Densitometry of images was then done using NIH Image 1.62 software. Data are graphed as a percentage of growth factor (EGF, VEGF) treated controls. As can be seen in FIGS. 4a and 4b, ZY/AG-91 provided excellent inhibition of both EGFR and Flk1 tyrosine kinase activity.

Example 7

Additional data from the phospho-EGFR and Flk1 assays are presented in Tables 1 (EGFR kinase inhibition), Table 2 (Flk1 kinase inhibition), Table 3 (A431 cytotoxicity) and Table 4 (comparative data showing EGFR, Flk-1, Flt-1 and PDGFR kinase inhibition, A431 cytotoxicity, U251 cytotoxicity inhibition and CAM angiogenesis inhibition. Table 1 identifies the compound, its structure, and the inhibitory concentration ($K_{50}$ (mM)) against EGFR kinase. The performance of these compounds was measured against PD153035 and SU5416, both of which are in clinical trials as anti-tumor agents. As can be seen in Table 1, compounds YJ/AG 176 had excellent inhibitory activity, and several other compounds had very good inhibitory activity as well. As can be seen in Tables 1, 2 and 3, many of the compounds tested had very low $IC_{50}$ values, comparable to compounds already known to provide significant inhibition of these enzymes such as PD15305 (Traxler, P. et al.) and SU5416 (Sun, L. et al.). As is understood by one skilled in the art, the lower the $IC_{50}$ value, the more potent the inhibition of the enzyme.

Table 4 provides comparative data indicating that many of the compounds have multiple modes of action.

TABLE 1
EGFR Kinase Inhibition
| Sample Number | Structure | IC$_{50}$($\mu$M) |
|---|---|---|
| YJ/AG 176 | 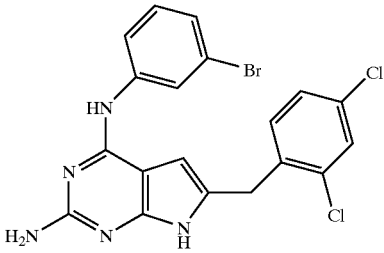 | 0.2 |
| YJ/AG 146 | 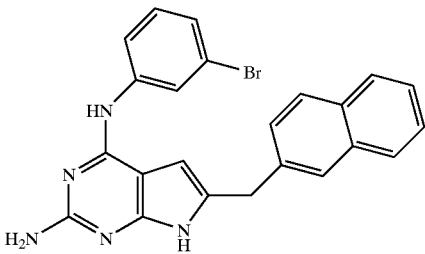 | 1.2 |
| YJ/AG 156 | 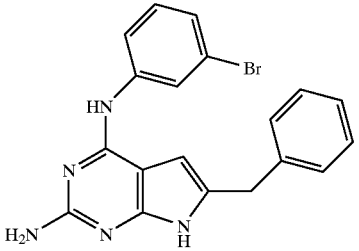 | 1.7 |
| YJ/AG 145 | 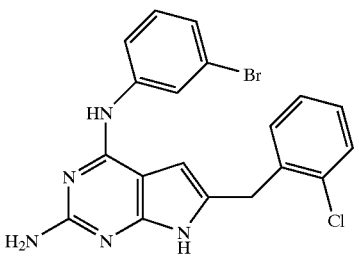 | 4.3 |
| YJ/AG 154 | 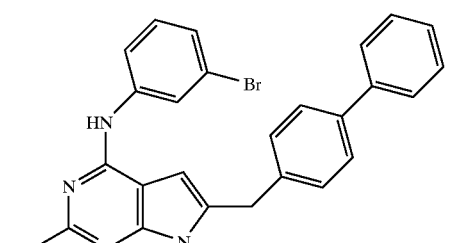 | 6.2 |

TABLE 1-continued
EGFR Kinase Inhibition
| Sample Number | Structure | IC$_{50}$($\mu$M) |
|---|---|---|
| YJ/AG 168 | 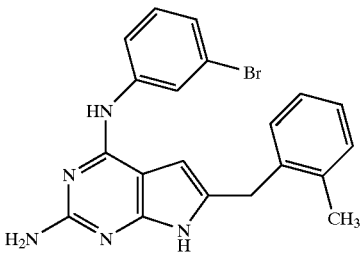 | 9.2 |
| YJ/AG 178 | 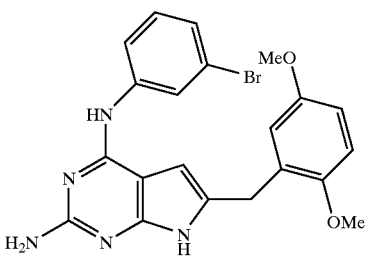 | 12.6 |
| YJ/AG 140 | 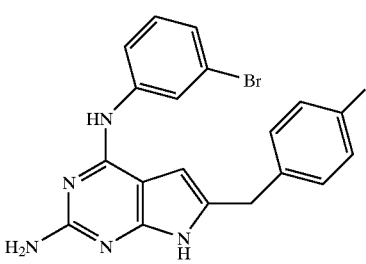 | 17.4 |
| YJ/AG 148 | 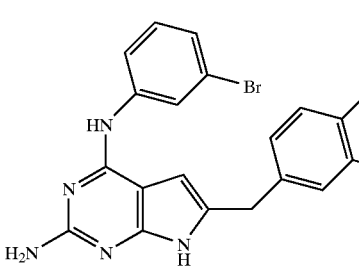 | 19.8 |
| YJ/AG 158 | 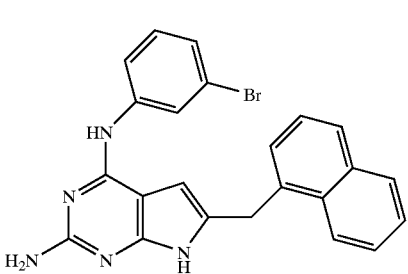 | >50 |

TABLE 1-continued
EGFR Kinase Inhibition
| Sample Number | Structure | IC$_{50}$(μM) |
|---|---|---|
| YJ/AG 177 | 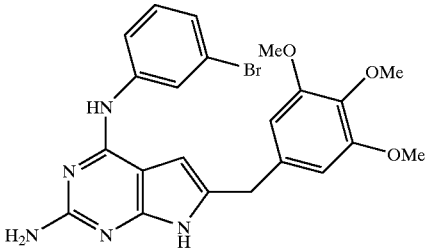 | >50 |
| PD153035 | | 0.2 |
| SU5416 | | ND |
TABLE 2
FlK1 Kinase Inhibition
| Sample Number | Structure | IC$_{50}$(μM) |
|---|---|---|
| YJ/AG 168 | 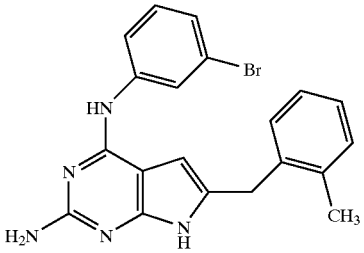 | 0.3 |
| YJ/AG 178 | 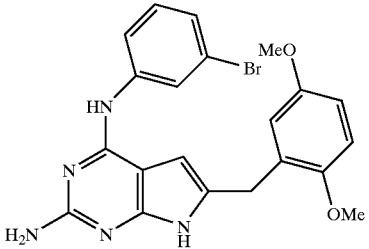 | 0.6 |
| YJ/AG 158 | 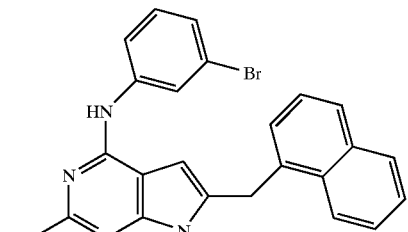 | 5.1 |

TABLE 2-continued

FIK1 Kinase Inhibition

| Sample Number | Structure | IC$_{50}$($\mu$M) |
|---|---|---|
| YJ/AG 145 | 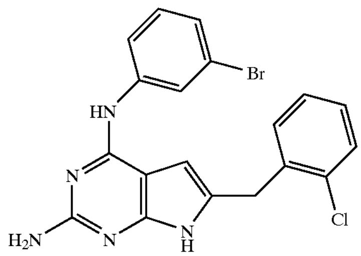 | 5.6 |
| YJ/AG 154 | 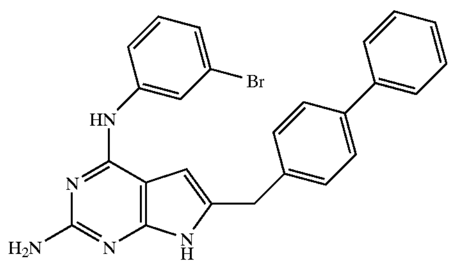 | 6 |
| YJ/AG 177 | 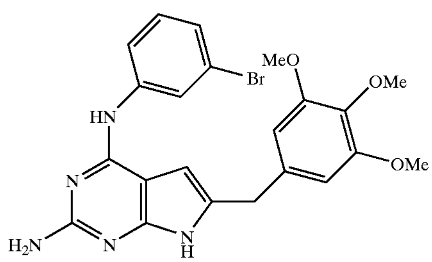 | 9.4 |
| YJ/AG 176 | 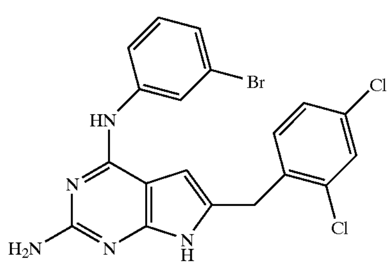 | 28.1 |
| YJ/AG 140 | 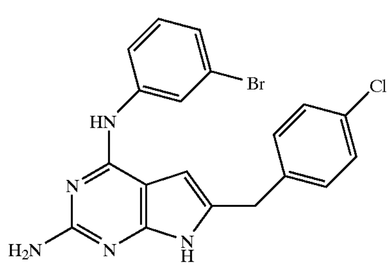 | ND |

TABLE 2-continued
FIK1 Kinase Inhibition
| Sample Number | Structure | IC$_{50}$($\mu$M) |
|---|---|---|
| YJ/AG 146 | 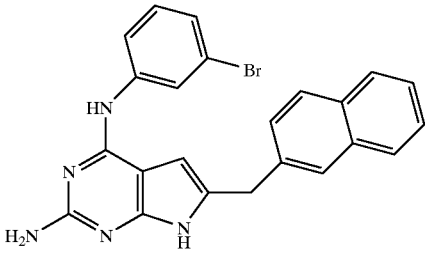 | >50 |
| YJ/AG 148 | 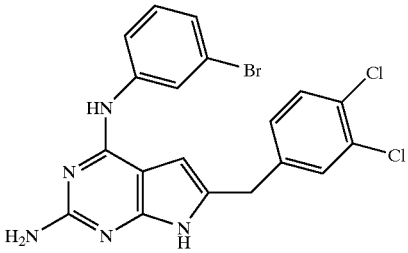 | >50 |
| YJ/AG 156 | 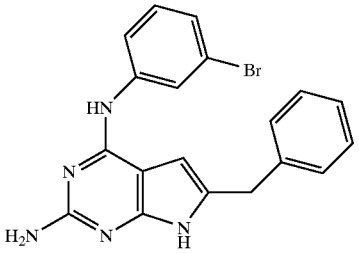 | >50 |
| PD153035 | | ND |
| SU5416 | | 2.4 |
TABLE 3
A4311 Cytotoxicity
| Sample Number | Structure | IC$_{50}$($\mu$M) |
|---|---|---|
| YJ/AG 168 | 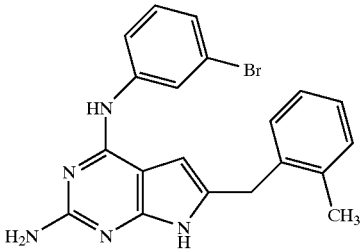 | 1.2 |

TABLE 3-continued
A4311 Cytotoxicity
| Sample Number | Structure | IC$_{50}$($\mu$M) |
|---|---|---|
| YJ/AG 176 | 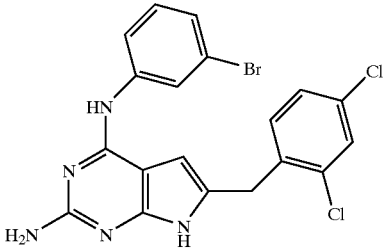 | 2.8 |
| YJ/AG 154 | 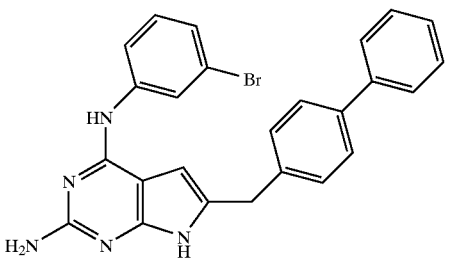 | 23.5 |
| YJ/AG 146 | 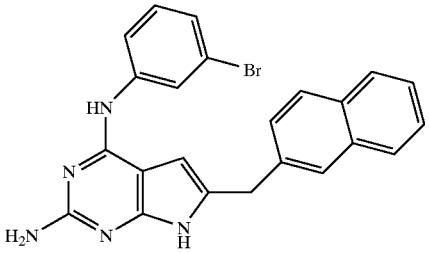 | 33.2 |
| YJ/AG 148 | 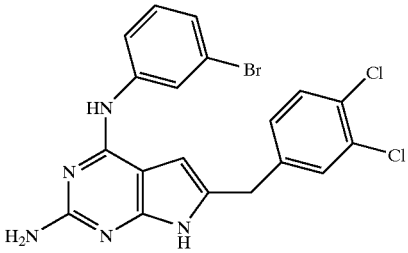 | 33.5 |
| YJ/AG 177 | 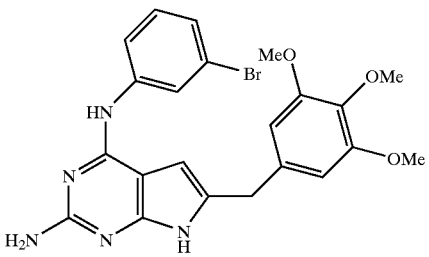 | 42.1 |

TABLE 3-continued

A4311 Cytotoxicity

| Sample Number | Structure | IC$_{50}$($\mu$M) |
|---|---|---|
| YJ/AG 140 | 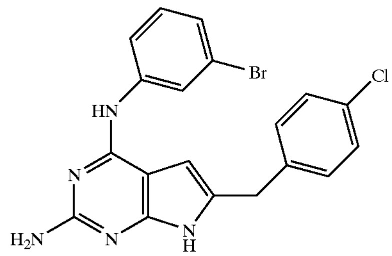 | ND |
| YJ/AG 145 | 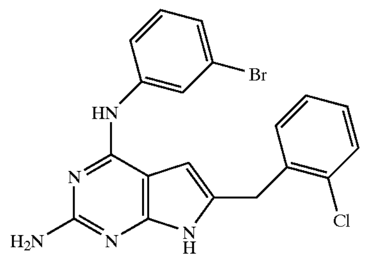 | >50 |
| YJ/AG 158 | 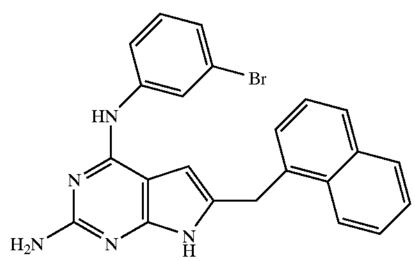 | >50 |
| YJ/AG 178 | 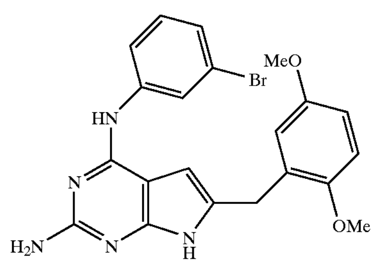 | >50 |
| YJ/AG 156 | 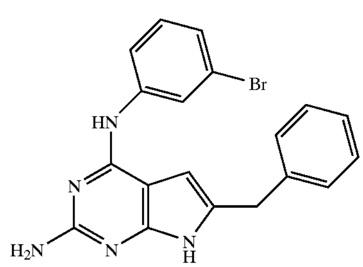 | >50 |
| PD153035 | | 12.6 |
| SU5416 | | 19.2 |

TABLE 4

Apparent IC50 (μM) values of AG compounds 9/01

| | EGFR kinase Inhibition | Flk-1 kinase Inhibition | Flt-1 kinase Inhibition | PDGFR kinase Inhibition | A431 cyto-toxicity | U251 cytotoxicity Inhibition | CAM angiogenesis Inhibition |
|---|---|---|---|---|---|---|---|
| COMPOUND | | | | | | | |
| YJ/AG 140 | 17.4 | ND | ND | ND | ND | | ND |
| YJ/AG 145 | 4.3 | 5.6 | 26.8 | >50 | >50 | | 1.7 |
| YJ/AG 146 | 1.2 | >50 | 15.2 | >50 | 33.2 | | 8.9 |
| YJ/AG 148 | 19.8 | >50 | >50 | >50 | 33.5 | | <0.1 (toxic) |
| YJ/AG 154 | 6.2 | 6.0 | ND | ND | 23.5 | | <0.1 |
| YJ/AG 156 | 1.7 | >50 | >50 | >50 | 31.8 | 3.4 | <0.1 |
| YJ/AG 158 | >50 | 5.1 | 19.2 | >50 | >50 | | <0.1 |
| YJ/AG 168 | 9.2 | 0.3 | >50 | >50 | 1.2 | 5.0 | 1.2 |
| YJ/AG 176 | 0.2 | 28.1 | >50 | 17.0 | 2.8 | | 10.8 |
| YJ/AG 177 | >50 | 9.4 | >50 | 14.7 | 42.1 | | 0.4 |
| YJ/AG 178 | 12.6 | 0.6 | 31.1 | 8.9 | >50 | | 1.3 |
| ZY/AG 70-1 | >50 | 12.8 | >50 | 10.3 | >50 | | <0.1 |
| ZY/AG 91 | >50 | 2.8 | >50 | 8.6 | >50 | 1.8 | <0.1 |
| JY/AG 149 | 2.2 | 18.4 | | | 3.6 | | |
| JY/AG 260 | 0.3 | >50 | | | 28.6 | | |
| JY/AG 263 | 1.6 | 25.3 | | | 38.9 | | |
| JY/AG 274 | 2.2 | >50 | | | >50 | >50 | |
| JY/AG 275 | 3.4 | 42.3 | | | 13.2 | | |
| JY/AG 276 | 0.3 | 49.9 | | | 19.6 | | |
| JY/AG 282 | 4.7 | 16.8 | | | >50 | | |
| JY/AG 283 | 4.8 | ND | | | 8.2 | | |
| POSITIVE CONTROLS | | | | | | | |
| PD153035 | 0.2 | | | | 12.6 | | |
| SU5416 | | 2.4 | | | 19.2 | 0.2 | <0.1 |
| cisplatin | | | | | 8.2 | 4.2 | |
| VEGF kinase Inhibitor | | | 17.7 | | | | |
| AG1295 | | | | | 6.2 | | |

NOTES:
1. ND = not determined
2. Nomenclature: compound numbers include only the LAST number of sample (E.G., JY/AG 113–282 = JY/AG 282)
3. A431 cells overexpress the EGFR; U251 cells overexpress Flk1 and PDGFRbeta; HT29 cells do not express EGFR, Flk1, Flt1, or PDGFR at measurable levels Whereas particular embodiments of this invention have been described above for purposes of illustration, it will be evident to those skilled in the art that numerous variations of the details of the present invention may be made without departing from the invention as defined in the appended claims.

What is claimed is:

1. A compound, and pharmaceutically acceptable salts, solvates and prodrugs thereof, having the formula (3):

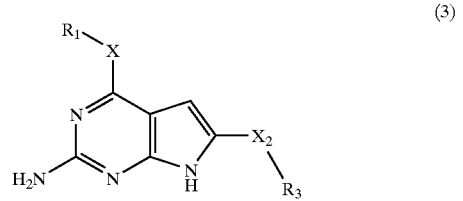

(3)

where X is NII— and $R_1$ is present;

$X_2$ is from one to three atoms, and if $R_3$ is not present, is independently selected from the group consisting of hydrogen, an alkyl group, an alkenyl group, a heteroalkyl group and a heteroalkenyl group, and if $R_3$ is present, $X_2$ is selected from the group consisting of an alkenyl group, a heteroalkylene group, an alkenylene group, and a heteroalkenylene group;

and any carbons or nitrogens of said alkyl group, alkylene group, alkenyl group, alkenylene group, heteroalkylene group, hetroalkylene group, heteroalkenylene group or heteroalkenyl group can optionally be substituted with a straight or branched lower alkyl group or alicyclic group of from 1 to 6 carbons;

$R_3$ is optionally present;

$R_1$ is selected from the group consisting of an alicyclic group, a heterocyclic group, an aryl group, a heteroaryl group, an alkylaryl group, a alkylheteroaryl group, a substituted aryl group, a substituted heteroaryl group, a substituted alkylaryl group and a substituted alkylheteroaryl group;

if present, $R_3$ is selected from group consisting of hydrogen, an alicyclic group, a heterocyclic group, an aryl group, a heteroaryl group, an alkylaryl group, a alkylheteroaryl group, a substituted aryl group, a substituted heteroaryl group, a substituted alkylaryl group, a substituted alkylheteroaryl group, and a 4-(1,3-dicarboxyl propyl amino carbonyl) aryl group;

and each substituent of any substituted group is the same or different and is selected from the group consisting of a straight or branched lower alkyl, alkenyl, alkynl or alicyclic group of from one to 6 carbons, an alkoxy group, an alkoxyaryloxy group, and a halogen.

2. The compound of claim 1, wherein $R_1$ is m-bromophenyl.

3. The compound of claim 1, wherein $X_2$ is $CH_2$—$CH_2$.

4. The compound of claim 3, wherein $R_3$ is 2-pyridyl.

5. The compound of claim 3, wherein $R_3$ is phenyl.

6. The compound of claim 3, wherein $R_3$ is p-methoxyphenyl.

7. The compound of claim 3, wherein $R_3$ is o-chlorophenyl.

8. The compound of claim 3, wherein $R_3$ is 1-naphthyl.

9. The compound of claim 3, wherein $R_3$ is 2-naphthyl.

10. The compound of claim 1, wherein $X_2$ is $CH_2$—.

11. The compound of claim 10, wherein $R_3$ is phenyl.

12. The compound of claim 10, wherein $R_3$ is 2-methylphenyl.

13. The compound of claim 10, wherein $R_3$ is 2-chlorophenyl.

14. The compound of claim 10, wherein $R_3$ is 2,4-dichlorophenyl.

15. The compound of claim 10, wherein $R_3$ is 2,5-dimethoxyphenyl.

* * * * *

UNITED STATES PATENT AND TRADEMARK OFFICE
CERTIFICATE OF CORRECTION

PATENT NO. : 6,770,652 B2
DATED : August 3, 2004
INVENTOR(S) : Aleem Gangjee

It is certified that error appears in the above-identified patent and that said Letters Patent is hereby corrected as shown below:

Title page,
Item [56], References Cited, OTHER PUBLICATIONS, "Learning for Angiogenesis Trial Failures" reference, "for" should read -- from --.
Item [57], ABSTRACT, delete the "," after "pounds".

Column 3,
Line 17, "an" should read -- a --.

Column 5,
Line 50, insert -- the -- prior to the first occurrence of "group".

Column 27,
Line 62, "NII" should read -- NH --.

Column 28,
Line 58, insert -- the -- prior to "group".
Line 63, delete "a 4-(1,3-dicarboxyl propyl amino carbonyl) aryl group;" insert -- *p*-aroyl-glutamate; --.

Signed and Sealed this

Fifth Day of April, 2005

JON W. DUDAS
*Director of the United States Patent and Trademark Office*